(12) United States Patent
Gura et al.

(10) Patent No.: US 7,828,761 B2
(45) Date of Patent: Nov. 9, 2010

(54) WEARABLE ULTRAFILTRATION DEVICE

(75) Inventors: Victor Gura, Beverly Hills, CA (US);
Edmond Rambod, Los Angeles, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 496 days.

(21) Appl. No.: 11/830,695

(22) Filed: Jul. 30, 2007

(65) Prior Publication Data

US 2008/0021366 A1    Jan. 24, 2008

Related U.S. Application Data

(63) Continuation of application No. 10/251,937, filed on Sep. 19, 2002, now Pat. No. 7,597,677, which is a continuation-in-part of application No. 10/085,349, filed on Nov. 16, 2001, now Pat. No. 6,960,179.

(51) Int. Cl.
*A61M 37/00* (2006.01)
*C02F 1/44* (2006.01)

(52) U.S. Cl. .................. 604/5.04; 604/6.09; 604/6.1; 604/6.11; 210/645; 210/195.2; 210/433.1; 210/416.1; 210/500.21

(58) Field of Classification Search ................ 604/6.09, 604/6.11, 5.01, 5.04, 6.15, 6.16; 210/645–646, 210/600, 634, 644, 195.2, 416.1, 433.1, 321.71, 210/500.21, 258, 259; 422/44
See application file for complete search history.

(56) References Cited

U.S. PATENT DOCUMENTS

| 3,388,803 | A | 6/1968 | Scott |
| 3,746,175 | A | 7/1973 | Markley |
| 3,884,808 | A | 5/1975 | Scott |
| 3,994,799 | A | 11/1976 | Yao et al. |
| 4,094,775 | A | 6/1978 | Mueller |
| 4,212,738 | A | 7/1980 | Henne |
| 4,247,393 | A | 1/1981 | Wallace |
| 4,267,040 | A | 5/1981 | Schal |
| 4,269,708 | A | 5/1981 | Bonomini et al. |
| 4,443,333 | A | 4/1984 | Mahurkar |
| 4,563,170 | A | 1/1986 | Aigner |
| 4,765,907 | A * | 8/1988 | Scott .................... 210/648 |
| 4,897,189 | A | 1/1990 | Greenwood et al. |
| 4,997,570 | A | 3/1991 | Polaschegg |
| 5,284,470 | A | 2/1994 | Beltz |
| 5,391,143 | A | 2/1995 | Kensey |

(Continued)

OTHER PUBLICATIONS

Roberts, Martin, "Wearable Artificial Kidneys for Continuous Dialysis," ASAIO Journal, 1993, pp. 19-23.

(Continued)

*Primary Examiner*—Leslie R Deak
(74) *Attorney, Agent, or Firm*—Hamilton, Brook, Smith & Reynolds, P.C.

(57) ABSTRACT

An ultrafiltration device adapted to be worn on a portion of the body of a patient includes a blood inlet tube leading from a first blood vessel, a blood pump, an anticoagulant reservoir for infusing anticoagulants into the blood, a blood filter including a substrate through which the blood is circulated and filtered, a fluid bag for storing the excess fluid and a blood outlet tube leading to a second blood vessel.

16 Claims, 2 Drawing Sheets

U.S. PATENT DOCUMENTS

| | | | |
|---|---|---|---|
| 5,415,532 A * | 5/1995 | Loughnane et al. | 417/411 |
| 5,545,131 A | 8/1996 | Davankov | |
| 5,902,336 A | 5/1999 | Mishkin | |
| 5,944,684 A | 8/1999 | Roberts et al. | |
| 5,984,891 A | 11/1999 | Keilman et al. | |
| 6,117,122 A | 9/2000 | Din et al. | |
| 6,196,992 B1 | 3/2001 | Keilman et al. | |
| 6,332,985 B1 | 12/2001 | Sherman et al. | |
| 6,561,996 B1 * | 5/2003 | Gorsuch | 604/6.09 |
| 6,632,192 B2 | 10/2003 | Gorsuch et al. | |
| 6,685,664 B2 | 2/2004 | Levin et al. | |
| 6,796,955 B2 | 9/2004 | O'Mahony et al. | |
| 6,890,315 B1 * | 5/2005 | Levin et al. | 604/6.09 |
| 2002/0107469 A1 * | 8/2002 | Bolan et al. | 604/6.01 |

OTHER PUBLICATIONS

Murisasco, A. et al., "Continuous Arterio-venous Hemofiltration in a Wearable Device to Treat End-stage Renal Disease," Trans Am Soc Artif Intern Organs, vol. XXXII, 1986, pp. 567-571, 1986.

Murisasco, A. et al., "A Continuous Hemofiltration System Using Sorbents for Hemofiltrate Regeneration," Clinical Nephrology, vol. 26, Supp. No. 1, 1986, pp. S53-S57.

Lande', Arnold J. et al., "In Search of a 24 Hours Per Day Artificial Kidney," Journal of Dialysis, 1(8), 1977, pp. 805-823.

Manns, Markus et al., "The acu-men: A new device for continuous renal replacement therapy in acute renal failure," Kidney International, vol. 54, 1998, pp. 268-274.

* cited by examiner

WEARABLE ULTRAFILTRATION DEVICE

REFERENCE TO RELATED APPLICATIONS

This application is a continuation of U.S. patent application Ser. No. 10/251,937, filed Sep. 19, 2002, and entitled WEARABLE ULTRAFILTRATION DEVICE, now U.S. Pat. No. 7,597,677, issued Oct. 6, 2009. U.S. Pat. No. 7,597,677 is incorporated by reference in its entirety into this application. U.S. patent application Ser. No. 10/251,937 is a continuation-in-part of U.S. patent application Ser. No. 10/085,349, filed Nov. 16, 2001 and entitled WEARABLE CONTINUOUS RENAL REPLACEMENT THERAPY DEVICE, now U.S. Pat. No. 6,960,179, issued on Nov. 1, 2005. U.S. Pat. No. 6,960,179 is incorporated by reference in its entirety into this application.

TECHNICAL FIELD

The present invention is directed to ultrafiltration devices, and more particularly to a portable ultrafiltration device that may be continuously worn by a patient.

BACKGROUND

Fluid overload can be caused by many things including metabolic disease, renal failure and, especially, congestive heart failure (CHF), which has become a disease of epidemic proportions all over the globe. CHF is a progressive deterioration of the heart muscle that leads to an inability to pump enough blood to support the vital organs. Deterioration of the heart muscle leads to decreased pumping capacity and increased fluid retention caused by the lack of perfusion pressure of the kidneys due to the failure of the heart to pump enough blood at the proper pressure. Fluid overload can cause leg swelling, shortness of breath and water accumulation in the lungs, impairing the ability to properly breathe.

Removal of excess fluids from the body can be accomplished with diuretics and other drugs that improve the performance of the heart muscle. However, these drugs become gradually ineffective over time and may cause undesirable effects such as kidney failure. In addition, there is a growing body of research supporting the notion that fluid removal by ultrafiltration may be superior to the administration of very large doses of diuretic drugs.

Advantages of ultrafiltration over diuretic drugs include: (1) efficient fluid removal without side effects such as kidney failure and blood pressure drops; (2) prompt relief form shortness of breath and swelling; and (3) improvement regarding certain adverse hormonal effects that are associated with CHF.

Ultrafiltration is performed by pumping blood from a catheter in an artery or a large vein, though a blood filter or a dialyzer, while creating a gradient of pressure though the filter membrane. The pressure gradient forces the passage of fluid out of the blood by convection and the fluid is drained out.

Conventional ultrafiltration devices suffer from several drawbacks. Usually, these devices are cumbersome, heavy and must be hooked to electrical outlets. Since ultrafiltration patients must remain connected to these devices for many hours, their ability to perform normal every day activities is severely limited. In addition, typical ultrafiltration treatments are geared for fast removal of several liters of excess fluid. However, the fluid removal is only temporary and the excess fluid usually reaccumulates in the patient's body after a short period of time. The reaccumulation of fluid is harmful to the patients, as the kidneys are further injured by the progress of CHF and the side effects of the diuretic drugs used to treat the heart.

A further problem with ultrafiltration devices is that repeated reconnection to an ultrafiltration device requires accessing blood flow by puncturing a large blood vessel and forming an arteriovenous shunt. These shunts only last for limited periods of time and are subject to infection, clotting and other complications that result in numerous hospitalizations and repeated surgical interventions. Similar problems also exist when a patient's blood stream is accessed by alternative methods, such as by inserting large catheters into large veins and arteries.

In view of the above disadvantages, there is a substantial need for a portable ultrafiltration device that provides continual, steady and smooth removal of excess fluid from the body.

SUMMARY

The present invention alleviates to a great extent the above-noted and other disadvantages by providing a portable, wearable ultrafiltration device that performs continuous, steady and smooth removal of excess fluid from the body. Importantly, this ultrafiltration device does not require a patient to be hooked up to a large machine for many hours a day, several days per week. Instead, the ultrafiltration device can conveniently be worn on a patient's body for continual use, 24 hours a day, seven days a week, providing steady and smooth removal of excess fluid from the body and preventing the shortness of breath and swelling that are associated with CHF.

One aspect of the present invention involves an ultrafiltration device adapted to be worn on a portion of the body of a patient, including a blood pump and a blood filter for separating excess fluid from the blood.

A further aspect of the present invention involves an ultrafiltration device in the form of a belt adapted to be worn about the waist, shoulder, thigh or other body portion of a patient, wherein the belt includes a pair of end portions which are secured together by a belt fastening means.

Another aspect of the present invention involves an ultrafiltration device adapted to be worn on a portion of the body of a patient includes a blood inlet tube leading from a first blood vessel, a blood pump, an anticoagulant reservoir from which anticoagulants are infused into the blood, a blood filter including a substrate through which the blood is circulated and filtered, a fluid bag for storing the excess fluid and a blood outlet tube leading to a second blood vessel.

These and other features and advantages of the present invention will be appreciated from review of the following detailed description of the invention, along with the accompanying figures in which like reference numerals refer to like parts throughout.

BRIEF DESCRIPTION

DETAILED DESCRIPTION

Ultrafiltration is a process by which excess fluid in the form of water is removed from the blood, wherein the excess fluid in the blood is moved from one side of a filtering device to another. The filtering device contains many hollow fibers made out of a semipermeable membrane. While blood flows inside of the hollow fibers, water from the blood moves through the membrane wall and is drained off. The purified blood remains inside the hollow fibers and is returned to the body.

Figure 1:
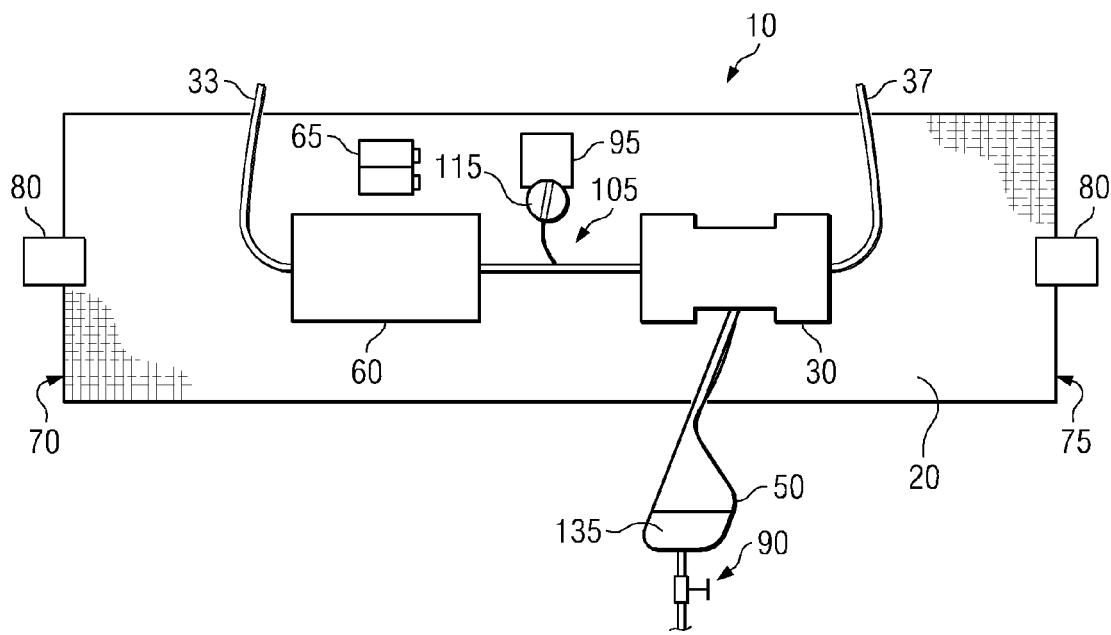
FIG. 1 is a perspective view of an embodiment of an assembly in accordance with the present invention.

Referring to FIG. 1, an ultrafiltration device 10 is designed to extract a targeted volume of fluid from the blood of a patient at a precisely controlled rate. The ability to predictably remove excess fluid from the blood reduces the risk of removing too much fluid too quickly, which can result in low blood pressure and vital organ damage.

The ultrafiltration device 10 comprises a belt 20 adapted to be worn about a portion of the body of the patient. According to some embodiments, the ultrafiltration device 10 is adapted to be worn about the waist of the patient. However, as would be understood to those of ordinary skill in the art, the device 10 may also be worn about other portions of the patient's body, such as over a shoulder or around a thigh. According to some embodiments, the weight of the belt 30 is less than two pounds.

As seen in FIG. 1, the belt 20 includes a pair of end portions 70, 75, which are secured together by a belt fastening means 80 such as a buckle 80, snaps 80, buttons 80 or hook and loop fasteners 80. The belt 20 further includes a blood filter 30 including a blood inlet tube 33 leading from a first blood vessel and a blood outlet tube 37 leading to a second blood vessel in the patient. The belt 20 also includes a blood pump 60, which forces the patient's blood through the filter 30. The pump 60 may be a shuttle pump, piston pump, roller pump, centrifuge pump, piezoelectric pump, or other convention pump. Convention power sources 65 such as batteries 65 can be use to power the blood pump 60.

The blood filter 30 separates excess fluid from the patient's blood. The excess fluid is drained in to an excess fluid bag 50, which is to be periodically emptied via tap 90. The fluid bag 50 can be positioned in the vicinity of a thigh, a leg, an ankle, an arm, or any other suitable body portion of the patient.

The coagulation of the blood circulating through the device 10 is prevented by the constant infusion of anticoagulant, which is infused from an anticoagulant reservoir 95 through a port 105 and into the blood inlet tube 33. In some embodiments, anticoagulant is infused using a battery powered anticoagulant pump 115. The pump 115 may be a shuttle pump, piston pump, roller pump, centrifuge pump, piezoelectric pump, or other convention pump. Typical anticoagulants are infused into the blood 150 include, but are not limited to, heparin, prostacyclin, low molecular weight heparin, hirudin and sodium citrate. According to other embodiments, blood clotting inside the device 10 can be prevented by the oral administration of anticoagulent drugs including, but not limited to, coumadin.

Figure 2:
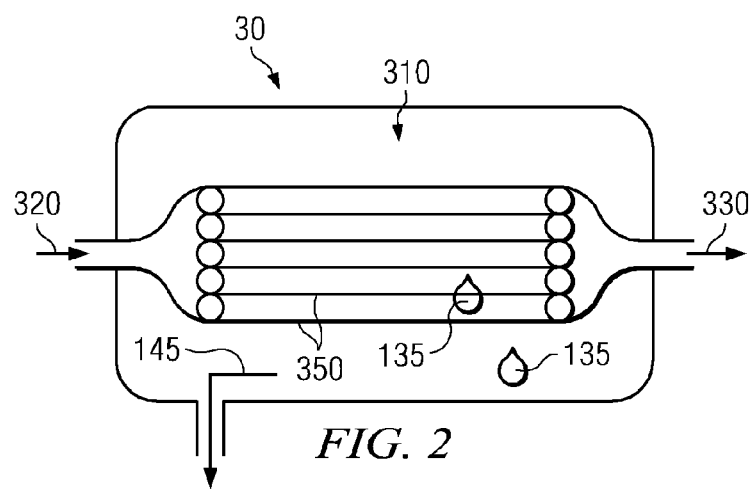
FIG. 2 is a perspective view of an embodiment of an assembly in accordance with the present invention.

Referring to FIG. 2, according to some embodiments, the blood filter 30 is a conventional blood filter 30 comprising a plurality of hollow fibers 310 through which the blood 150 is circulated. The exterior walls 350 of the hollow fibers 310 are semiporous so that excess fluid 135 in the form of water 135 and impurities 135 can be removed from the blood 150. As indicated by arrows 320, 330, excess fluid 135 is drained from the hollow fibers 310, which act as a sieve such that excess fluid 135 passes through, but not blood 150. The excess fluid 135 is drained out of the filter 30 in a direction indicated by arrow 145.

The blood 150 moves through the hollow fibers 310 under pressure from the blood pump 60. This pressure causes the excess fluid 135 in the blood 150 to filter out through the fiber pores, into the other side of the hollow fibers 310, from where the excess fluid 135 is drained out to the fluid bag 50. The magnitude of pressure within the fibers 310 determines the amount of net excess fluid 135 movement removed through exterior walls 350. Small particles within the blood 150 are also removed during this process, but particles larger than the blood filter pore size will be left behind in the blood 150.

Figure 3:
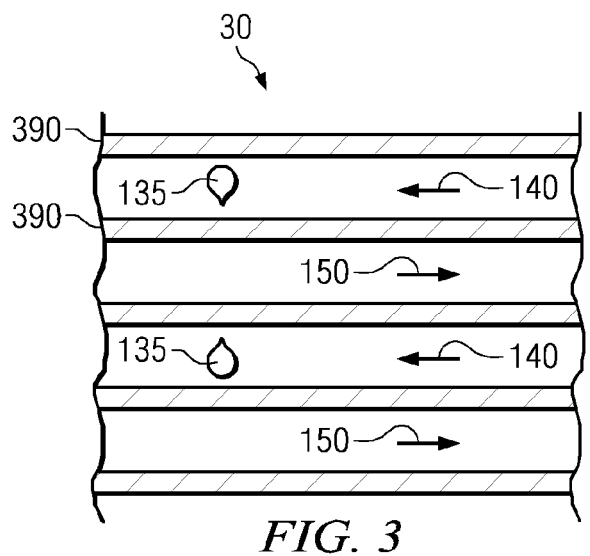
FIG. 3 is a perspective view of an embodiment of an assembly in accordance with the present invention.

Referring to FIG. 3, according to other embodiments, the blood filter 30 is an alternative conventional blood filter 30 comprising a plurality of parallel sheets 390 of semiporous material, wherein air 140 is circulated on one side of the parallel sheets 390 and the blood 150 circulates in the opposite direction on the other side of the parallel sheets 390. The blood filters 30 of these embodiments are conventional and well known in the art. Excess fluid 135 and small particles are removed from the blood 150 through parallel sheets 390 and drained off into excess fluid bag 50.

Figure 4:
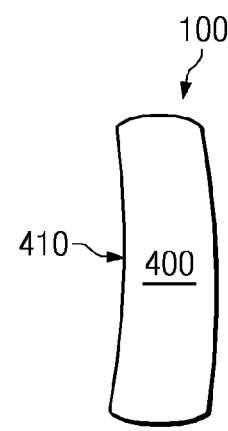
FIG. 4 is a perspective view of an embodiment of an assembly in accordance with the present invention.

Referring to FIG. 4, according to some embodiments, the blood filter 50 has a flexible casing 400 adapted to conform to the body contour of the patient. In addition, the body-side wall 410 of each casing 400 is concave to further correspond to bodily curves of the user. The casing 400 can be made of any suitable material having adequate flexibility for conformance to the portion of the body to which it is applied. Suitable materials include, but are not limited to polyurethane and poly vinyl chloride.

Figure 5:
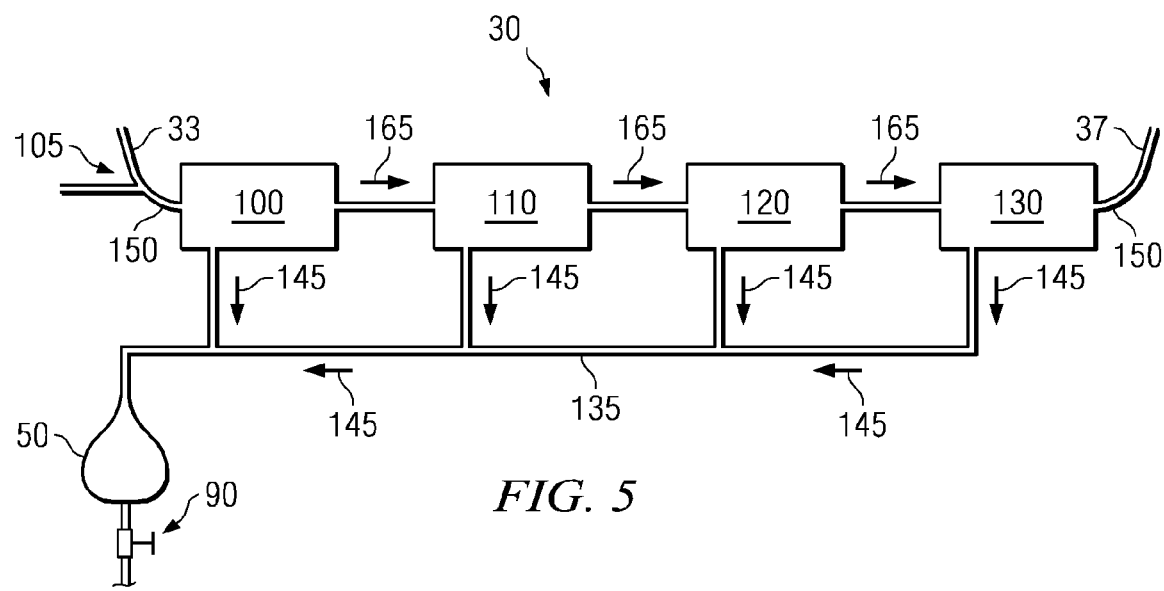
FIG. 5 is a perspective view of an embodiment of an assembly in accordance with the present invention.

Referring to FIG. 5, in an alternative embodiment, the blood filter 30 includes a plurality of miniaturized blood filters 100, 110, 120, 130 that remove impurities from the blood 150 of the patient. The number of filters, 110, 120, 130 in the plurality of filters, 110, 120, 130 may be varied to reflect different ultrafiltration prescriptions. The plurality of blood filters 100, 110, 120, 130 are connected in series, whereby the blood pump 60 forces the patient's blood 150, in a first direction, through the filters 100, 110, 120, 130, as indicated by arrows 165. Excess fluid 135 is drained from the blood filters 100, 110, 120, 130 and into the excess fluid bag 50 as indicated by arrows 145. As would be understood by those of ordinary skill in the art, the filters 100, 110, 120, 130 can also be connected in parallel without departing from the scope of the invention.

Thus, it is seen that a wearable ultrafiltration device is provided. One skilled in the art will appreciate that the present invention can be practiced by other than the preferred embodiments which are presented in this description for purposes of illustration and not of limitation, and the present invention is limited only by the claims that follow. It is noted that equivalents for the particular embodiments discussed in this description may practice the invention as well.

What is claimed is:

1. A method of ultrafiltrating excess body fluid from a congestive heart failure patient, the method comprising:
   obtaining, from a first blood vessel of a congestive heart failure (CHF) patient, blood containing excess body fluid;
   shuttle-pumping said blood with a shuttle pump;
   receiving at an ultrafiltration filter said blood;
   filtering the excess body fluid with said ultrafiltration filter to remove said excess body fluid from said blood at a rate slow enough to reduce a risk of creating a low blood pressure condition in said CHF patient and slow enough to allow continuous removal of said excess body fluid for at least 24 hours;

directing said removed excess body fluid directly to a fluid storage receptacle while the ultrafiltration filter is in various three-dimensional orientations; and returning said filtered blood to a second blood vessel of said CHF patient.

2. The method of claim 1, further comprising infusing an anticoagulant into said blood containing excess body fluid prior to filtering said blood containing excess body fluid.

3. The method of claim 1, wherein said shuttle pump, said ultrafiltration filter and said fluid storage receptacle are all completely wearable on said CHF patient.

4. The method of claim 1, further comprising filtering said blood containing excess body fluid for a period of time long enough to help deter the reaccumulation of excess body fluid in said CHF patient.

5. The method of claim 1, further comprising powering at least said shuttle pump with a wearable power source.

6. A method of ultrafiltrating excess body fluid from a congestive heart failure patient using a completely wearable ultrafiltration device, said method comprising:

receiving, in a blood inlet tube from a first blood vessel of a congestive heart failure patient, blood containing excess body fluid;

shuttle-pumping, with a shuttle pump included in said completely wearable ultrafiltration device, said blood containing excess body fluid from said blood inlet tube to an ultrafiltration filter, said ultrafiltration filter being included in said completely wearable ultrafiltration device;

separating an amount of excess body fluid from said blood containing excess fluid using said ultrafiltration filter, the combination of said shuttle pump and said ultrafiltration filter separate said amount of excess body fluid from said blood containing excess fluid at a rate slow enough to deter blood pressure drops in said CHF patient, at a rate slow enough to allow said completely wearable ultrafiltration device to continually operate for at least 24 hours, and at a rate fast enough to help alleviate the CHF patient's symptoms associated with CHF;

draining said separated excess fluid from said ultrafiltration filter to an excess fluid receptacle while the CHF patient performs a normal every day activity that places the completely wearable ultrafiltration device in random three-dimensional positions;

returning said filtered blood containing excess body fluid from said ultrafiltration filter to a second blood vessel of said CHF patient; and powering at least said shuttle pump with a power source, said power source being included in said completely wearable ultrafiltration device.

7. The method of ultrafiltrating excess body fluid from a CHF patient of claim 6, further comprising infusing an anticoagulant into said blood containing excess body fluid prior to separating said amount of excess body fluid from said blood.

8. The method of claim 7, wherein said infusing said anticoagulant comprises pumping said anticoagulant with an anticoagulant pump from an anticoagulant reservoir, said anticoagulant pump and said anticoagulant reservoir included in said completely wearable ultrafiltration device.

9. The method of claim 8, wherein said anticoagulant pump is a piston pump or a piezoelectric pump.

10. The method of claim 6, further comprising wearing said completely wearable ultrafiltration device on the body of said CHF patient continuously for a plurality of days.

11. The method claim 6, further comprising wearing said completely wearable ultrafiltration device about a shoulder of said CHF patient.

12. A method of removing excess body fluids from a CHF patient using a completely wearable, portable and self powered ultrafiltration device; said method comprises:

installing said completely wearable, portable and self powered ultrafiltration device on a CHF patient;

shuttle-pumping, from a first blood vessel of said CHF patient, fluid overloaded blood;

filtering excess body fluid, from said fluid overloaded blood, through a semiporous material at a rate that can be sustained for at least 24 hours without being a direct cause of a low blood pressure or damage to a vital organ in said CHF patient;

collecting said filtered excess body fluid directly after filtering and while the ultrafiltration device is in any three-dimensional position; and returning said filtered fluid overloaded blood to a second blood vessel of said CHF patient.

13. The method of claim 12, wherein said filtering excess body fluid through said semiporous material comprises creating a pressure gradient through said semiporous material.

14. The method of claim 12, wherein said installing said completely wearable, portable and self powered ultrafiltration device comprises installing said completely wearable, portable and self powered ultrafiltration device over said CHF patient's shoulder.

15. The method of claim 12, wherein said filtering of said excess body fluid is sustained for a period of time long enough to deter a reaccumulation of said excess body fluid in said CHF patient.

16. The method of claim 12, wherein collecting further comprises collecting said filtered excess body fluid by providing continuous flow availability from filtering to collecting.

* * * * *